(12) United States Patent
Baumann et al.

(10) Patent No.: US 9,532,010 B2
(45) Date of Patent: Dec. 27, 2016

(54) OBSERVATION INSTRUMENT WITH A SYMMETRICAL IMAGE FIELD GIVEN USE OF ASYMMETRIC IMAGE SENSORS

(71) Applicant: Karl Storz GmbH & Co. KG, Tuttlingen (DE)

(72) Inventors: Harald Baumann, Tuttlingen (DE); Peter Schwarz, Tuttlingen-Nendingen (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 373 days.

(21) Appl. No.: 14/307,045

(22) Filed: Jun. 17, 2014

(65) Prior Publication Data
US 2014/0368647 A1  Dec. 18, 2014

(30) Foreign Application Priority Data
Jun. 17, 2013 (DE) .................. 10 2013 106 278

(51) Int. Cl.
| | | |
|---|---|---|
| *H04N 7/18* | (2006.01) | |
| *A61B 1/00* | (2006.01) | |
| *A61B 1/05* | (2006.01) | |
| *G02B 23/24* | (2006.01) | |

(52) U.S. Cl.
CPC .............. *H04N 7/18* (2013.01); *A61B 1/00096* (2013.01); *A61B 1/00179* (2013.01); *A61B 1/051* (2013.01); *G02B 23/2446* (2013.01)

(58) Field of Classification Search
CPC ........................................................ H04N 7/18

USPC ........................................................... 348/143
See application file for complete search history.

(56) References Cited

U.S. PATENT DOCUMENTS

| | | | |
|---|---|---|---|
| 4,720,178 A | 1/1988 | Nishioka et al. | |
| 4,809,680 A | 3/1989 | Yabe | |
| 4,831,456 A | 5/1989 | Takamura | |
| 4,918,521 A | 4/1990 | Yabe et al. | |
| 2007/0030450 A1* | 2/2007 | Liang .................. | A61B 3/14 351/206 |

(Continued)

FOREIGN PATENT DOCUMENTS

| | | |
|---|---|---|
| DE | 3736688 A1 | 6/1988 |
| EP | 2719321 A1 | 4/2014 |
| JP | H09122071 A | 5/1997 |

*Primary Examiner* — Yulin Sun
(74) *Attorney, Agent, or Firm* — Whitmyer IP Group LLC

(57) ABSTRACT

An observation instrument has a hollow shaft in whose distal end region there is arranged an optoelectronic imaging system which has on the image entrance side a distal deflection prism whose deflection faces lead an image into an optical lens system which images the image onto the image plane of an image sensor arranged proximally from the lens system, the image sensor having an active region which is situated asymmetrically relative to the outer contour of the image sensor. A first plane, which is defined by the main beam and a first orthogonal on the image plane of the image sensor, and a second plane, which is defined by the main beam and a second orthogonal on the deflection faces of the distal deflection prism, being rotated relative to one another about the main beam in such a way that it is possible to produce a sight cone which is symmetrical relative to a midplane of the hollow shaft and whose image area is situated fully in the active region of the image sensor.

7 Claims, 5 Drawing Sheets

(56) References Cited

U.S. PATENT DOCUMENTS

2008/0091064 A1* 4/2008 Laser .................. A61B 1/053
600/109

* cited by examiner

OBSERVATION INSTRUMENT WITH A SYMMETRICAL IMAGE FIELD GIVEN USE OF ASYMMETRIC IMAGE SENSORS

BACKGROUND OF THE INVENTION

The invention relates to an observation instrument comprising a hollow shaft having a midplane and in whose distal end region there is arranged an optoelectronic imaging system which has on the image entrance side a distal deflection prism whose deflection faces lead an image into an optical lens system which images the image onto the image plane of an image sensor arranged proximally from the lens system, the image sensor having an active region which is situated asymmetrically relative to the outer contour of the image sensor.

Such an observation instrument in the form of a medical endoscope is known, for example, from U.S. Pat. No. 4,720,178 B2.

It is known from U.S. Pat. No. 4,809,680 that image sensors have an active region which is situated asymmetrically relative to the outer contour of the image sensor.

Image sensors usually exhibit a quadrangular, mostly a rectangular outer contour. For design reasons, in particular in order to accommodate the numerous electronic elements, the active region is situated asymmetrically, that is to say mostly offset laterally outwards. The active region likewise mostly has a rectangular contour.

Depending on the size ratios and the structural conditions within the shaft, such an image sensor can be installed vertically or tilted or horizontally.

If it is installed vertically, its image plane runs perpendicular to the longitudinal axis of the shaft. In tilted arrangements, said image plane is somewhat tilted to said longitudinal axis. Given horizontal installation, the image plane of the image sensor runs in the direction of the longitudinal axis and mostly in a fashion offset laterally parallel thereto.

Optimum utilization of the image information requires the image to be imaged onto the active region of the image sensor such that the image is situated within said active region. This is illustrated in FIG. 1. It is to be seen there that an image sensor 16 with an asymmetric active region 18 is installed vertically in a shaft 10. If the image area 20 is intended to be optimally detected by the active region 18, said image area mostly being circular, the main beam 21 of the optical path is situated in a fashion laterally offset from the middle longitudinal axis 14 of the shaft 10, and thus also in a fashion laterally offset from the midplane 12 thereof. This would also bring about the existence of an asymmetric sight cone of the observation instrument.

An asymmetric sight cone 22 as illustrated by way of example in FIG. 3 has certain disadvantages, however. Illustrated in FIG. 3 is a shaft 10 of an endoscope over which an overshaft 24 is pushed. Protruding from the distal end of the overshaft 24 are two rod-shaped elements 26 and 28 which are connected at the distal end via a resectoscope loop 30. In an asymmetric sight cone 22, because of the asymmetry of the sight cone 22 the observer sees two points 27 and 29, axially offset from one another, of the bars 26 and 28. This is undesirable, because the observer then sees the positions or, when the shaft 10 is shifted further in the distal direction, the resectoscope loop 30, not simultaneously or uniformly or out-of-focus on one side. Consequently, there is a desire for symmetrical sight cones 22, as is shown in FIG. 4. The viewpoints 27' and 29' are then situated at the same axial height in this stage.

However, as illustrated in FIG. 2, this can have the consequence that the image area 20 is no longer situated with its volume entirely in the active region 18 of the asymmetric image sensor 16 given a symmetrically designed imaging optics.

It is therefore an object of the present invention to provide an observation instrument in the case of which there is a sight cone which is as symmetrical as possible and the image is situated as completely as possible in the active region of the image sensor in the case of asymmetric image sensors.

SUMMARY OF THE INVENTION

The object is achieved according to the invention by an observation instrument, comprising a hollow shaft having a midplane and a distal end region, an optoelectronic imaging system arranged in said distal end region and having an image entrance side, a distal deflection prism having deflection faces, an optical lens system defining an optical path having a main beam, an image sensor having an image plane comprising an active region which is situated asymmetrically relative to an outer contour of said image sensor, said deflection faces of said distal deflection prism lead an image into said optical lens system which images said image onto said image plane of said image sensor, a first plane defined by the main beam and a first orthogonal on said image plane, and a second plane defined by said main beam and a second orthogonal on said deflection faces, wherein said first plane and said second plane being rotated relative to one another about said main beam to an extent to produce a sight cone of said optical lens system which is symmetrical relative to said midplane of said hollow shaft and whose image area is situated fully in said active region of said image sensor.

The rotation of said two planes relative to one another about the main beam has the effect that the active region of the asymmetric image sensor can be brought by said rotation into a position in which a sight cone symmetrical in relation to the midplane of the hollow shaft images an image in the active region. Owing to the interplay of the planes, which are determined, on the one hand, by the design of the distal deflection prism and, on the other hand, by the asymmetry of the image sensor, and to their rotation, it is now possible to allow the sight cone symmetrical to the midplane such that the problems mentioned at the beginning can no longer occur as they exist in conjunction with the resectoscope loop. On the other hand, owing to a corresponding relative rotation such a position between the planes has the result that said symmetrical sight cone images onto the active region, which is asymmetric relative to the outer contour of the image sensor.

In a further refinement of the invention, the image sensor is arranged vertically in the hollow shaft.

Said measure has the advantage that when mounting the vertically arranged image sensor it is possible to rotate about the middle longitudinal axis of the shaft until the image coming from the distal deflection prism is situated fully in the active region of the image sensor. It is thereby possible to produce a high-resolution image with optimum utilization of the resolution of the active region of the image sensor, which image permits a symmetrical sight cone.

In a further refinement of the invention, the image sensor is arranged tilted to the longitudinal axis of the shaft, and there is arranged between the proximal end of the lens system and the image sensor a proximal deflection prism which deflects the image emerging from the optical lens system onto the tilted image sensor.

This measure has the advantage that such image sensors can be installed even in relatively thin shafts.

In a further refinement of the invention, the image sensor is arranged horizontally and parallel to the longitudinal axis, and the proximal deflection prism effects a 90° deflection of the image.

This measure has the advantage that longitudinally extending rectangular image sensors can be installed even in extremely thin shafts.

In a further refinement of the invention, the first and the second planes are rotated relative to one another in such a way that the sight cone runs symmetrically relative to the shaft axis.

This measure has the advantage that a sight cone symmetrical relative to the center longitudinal axis or shaft axis is produced, in spite of the rotation of the planes. Such a sight cone having said high level of symmetry permits a panoramic view which determines an equally sharply focused image in all object planes.

In a further refinement of the invention, the image sensor is connected to an image processing unit by means of which the image which has been rotated by the rotation and, if appropriate, shifted is righted again laterally and in terms of height.

Owing to the rotation of the two planes relative to one another, the image is imaged onto the image sensor in a fashion rotated by the corresponding amount. Depending on how the first deflection prism is configured and on how the active region is situated in the image sensor, the image can also be appropriately shifted.

Since the image is mostly displayed on a monitor in modern operation technology, it is helpful for the operator to achieve his aim when he sees the image as it is present in the object field. This substantially facilitates the manipulation of the observation instrument by the operator.

In a further refinement of the invention, the optoelectronic imaging system is designed to produce a viewing direction deviating from the 0° viewing direction.

This measure has the advantage that a high-resolution image can be produced, in particular, when the viewing directions deviate from the 0° direction. In this respect, the distal deflection prism is provided to deflect the incoming image, which deviates from the 0° viewing direction, so that it is imaged as far as possible centrally on the mostly bar-shaped optical lens system. Thus, even given relatively large deviations from the 0° direction, that is to say 30°, 45° or 60°, for example, and simultaneous use of asymmetric image sensors it is still possible to produce very sharp and high-resolution images.

It goes without saying that the above named features, and those still to be explained below can be used not only in the specified combination, but also in other combinations without departing from the scope of the present invention.

The invention is described and explained in more detail with the aid of a few selected exemplary embodiments in conjunction with the attached drawings, in which:

DESCRIPTION OF PREFERRED EMBODIMENTS

Figure 5:
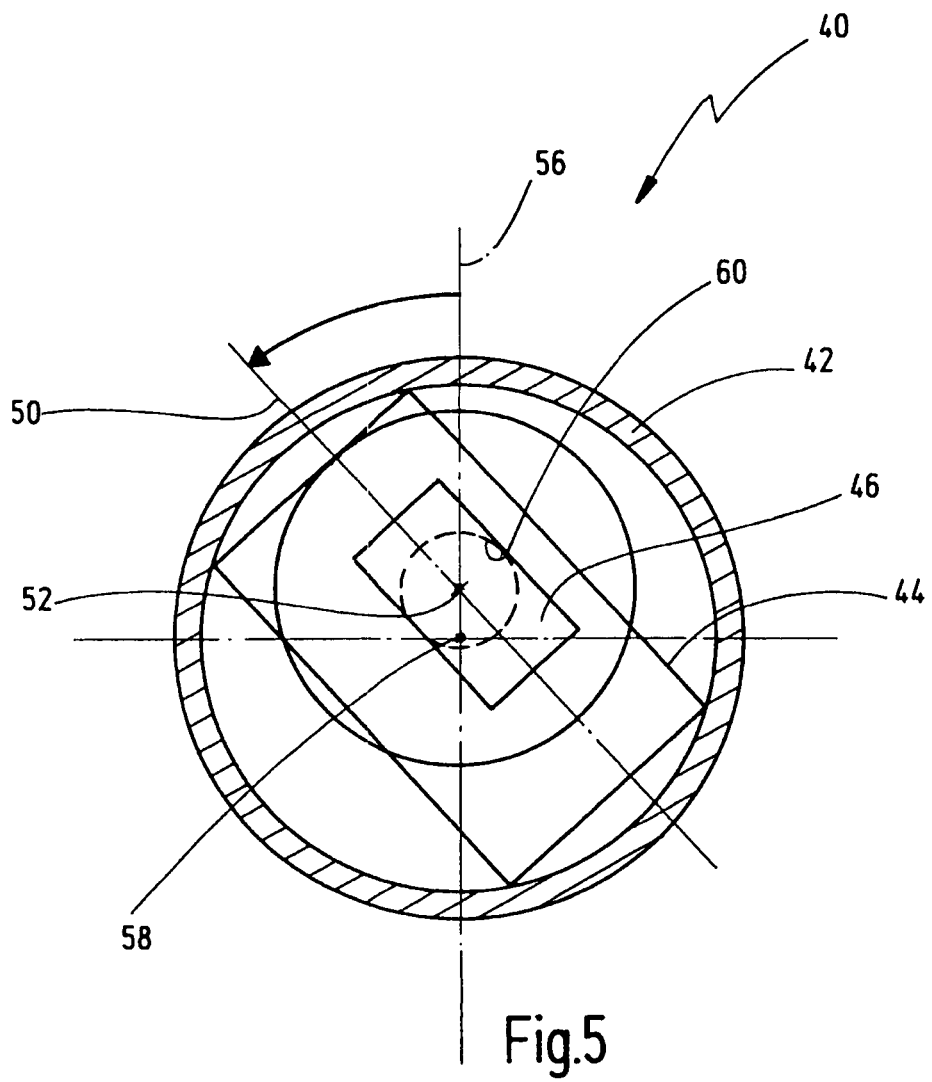
FIG. 5 shows a cross section through a shaft of a first exemplary embodiment of an observation instrument according to the invention with a vertically installed image sensor.

The basic principles of the invention are to be explained with the aid of the first exemplary embodiment, illustrated in FIG. 5, of an observation instrument 40 according to the invention. The observation system 40 has a shaft body 42 in which an image sensor 44 with a rectangular contour is installed vertically.

Figure 1:
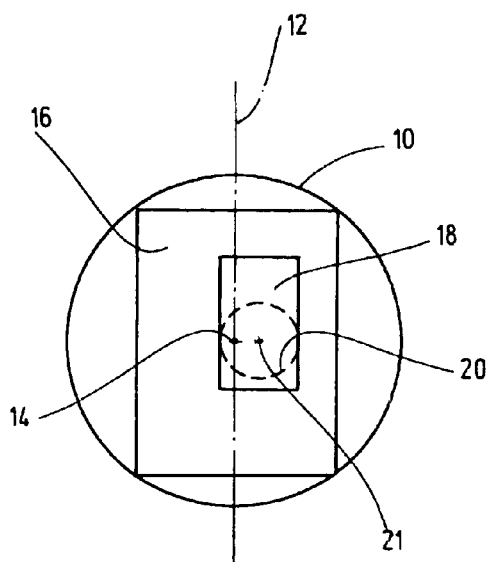
FIG. 1 shows very schematically a vertical installation of an asymmetric image sensor in a shaft, the image area being asymmetric in relation to the midplane and to the longitudinal axis.
Figure 2:
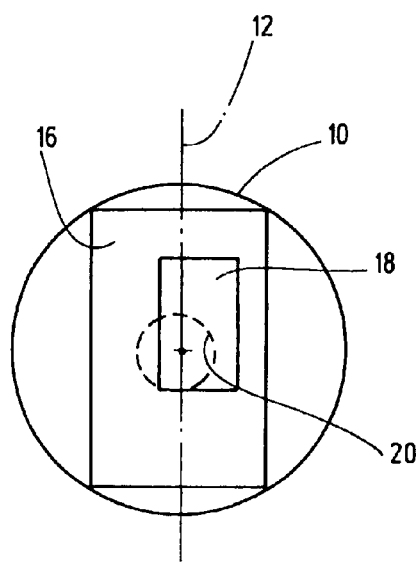
FIG. 2 shows an illustration in which in the same design the image area certainly runs symmetrically relative to the midplane and longitudinal axis of the shaft, but no longer fully impacts on the active region of the image sensor.
Figure 3:
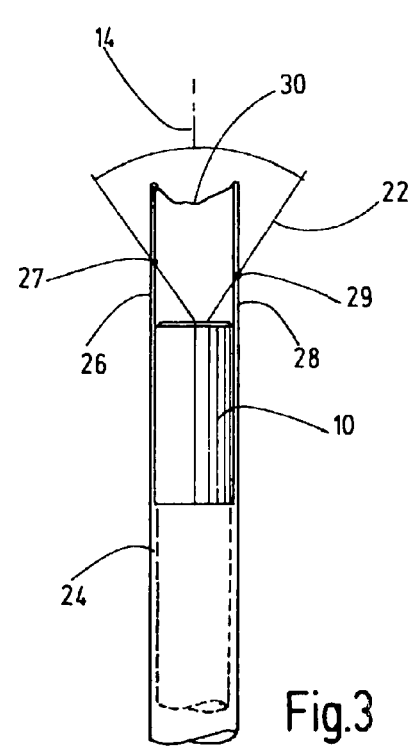
FIG. 3 shows very schematically a shaft for an endoscope with an asymmetric sight cone over which an overshaft with a resectoscope loop has been pushed.
Figure 4:
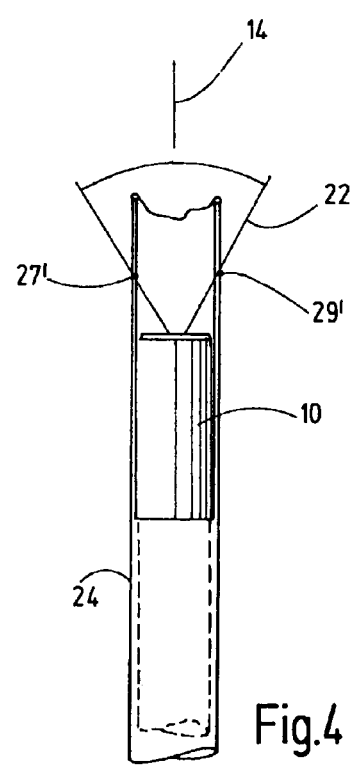
FIG. 4 shows a view, corresponding to FIG. 3, with a symmetrical sight cone.

The image sensor 44 has an active region 46 which is arranged asymmetrically relative to the outer contour of the image sensor 44. The shaft axis 58 is situated exactly in the middle of the shaft 42. In the illustration of FIG. 5, the main beam 52 is shifted somewhat upwards relative to the shaft axis 58 in the direction of the midplane 56. The first plane is defined by the main beam 52 and the orthogonal 50. The second plane is defined by the second orthogonal 56, which stands on the main beam 52. The active region 46 of the image sensor 44 is rotated anticlockwise relative to the shaft axis 58 to such an extent that the image area 60 is situated in the active region 46 of the image sensor 44. If the position of the image sensor illustrated in FIG. 2 is now compared with the position illustrated in FIG. 5, it is to be seen that the image area 60 is situated fully in the active region 46 owing to the rotation of the image sensor 44. The distal deflection prism (not visible here) produces in the lens system an image area 60 which is shifted upwards along the midplane 56, but symmetrically relative thereto. As illustrated in FIG. 4, it is possible to produce a symmetrical sight cone, and to obtain a high-resolution image fully in the middle of the active region 46 of the image sensor 44, but somewhat rotated and offset "upwards".

In a second exemplary embodiment illustrated in FIGS. 6 to 12, an observation instrument 70 is illustrated which has a shaft 72.

An optoelectronic imaging system 74 is accommodated in the distal end region 73 of the shaft 72.

The interior of the shaft 72 is divided into a first space 78 and a second space 80 by a transverse web 76.

Accommodated in the second space 80 is the illumination system, which is mostly light guides that output illuminating light 82 at the distal end from the second space 80.

The first space 78 is closed at the distal end by a cover glass 84. Adjoining said cover glass 84 is a lens 86 which is designed as a focusing lens. It is at the proximal end thereof in an entrance face of a distal deflection prism 88 that is inclined to the longitudinal axis 94 of the shaft 72. The distal deflection prism 88 has a first deflection face 90 and a second deflection face 92. Said faces are also denoted as mirror faces. As a result, a main beam 112 of an image of an object field 107 is guided centrally in the middle along the longitudinal axis 94 into an approximately bar-shaped lens system 96. Arranged at the proximal end of the lens system 96 is a proximal 90° deflection prism 98 whose exit face rests on an image sensor 100. The image sensor 100 is thus installed horizontally so that its active region 102 or its image plane 103 extends parallel to, and with slight spacing from the middle longitudinal axis 94 or to the main beam 112. As previously described, the active region 102 is arranged asymmetrically in relation to the outer contour of the somewhat rectangular image sensor 100.

Figure 6:
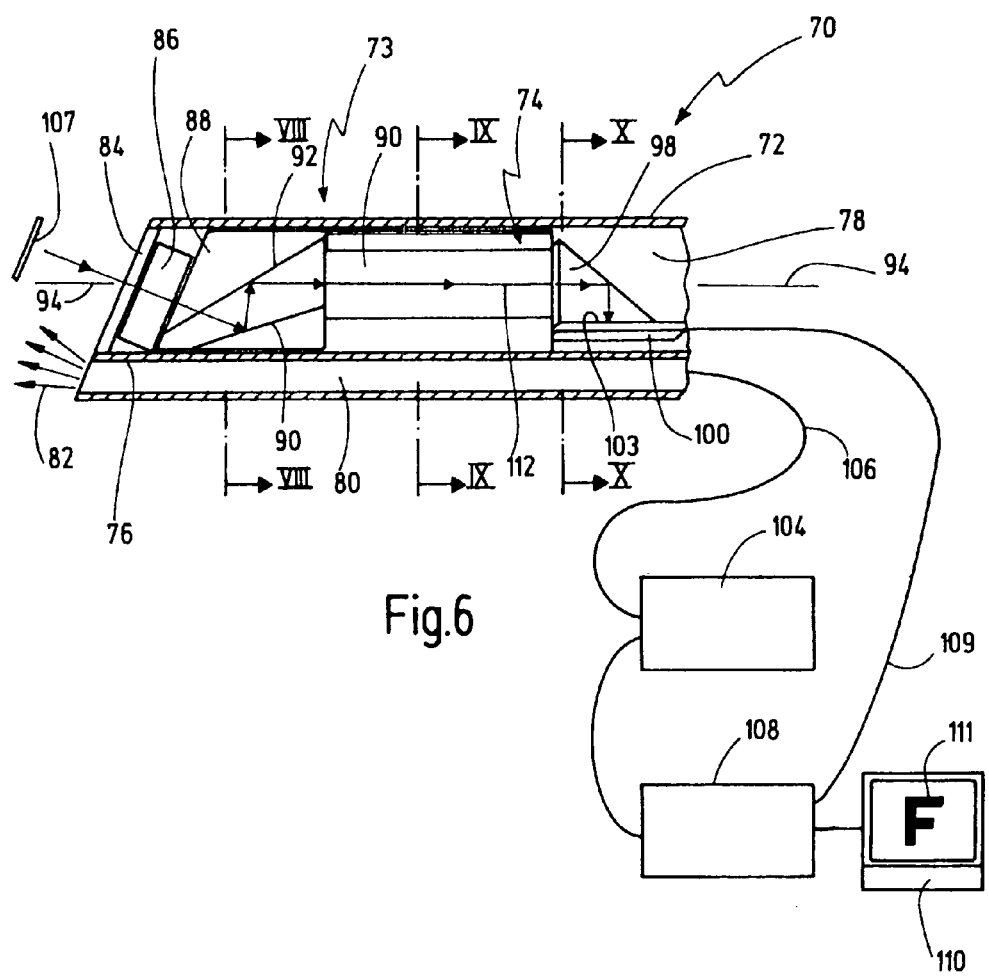
FIG. 6 shows a longitudinal section of a second exemplary embodiment of an observation instrument according to the invention in the distal end region thereof.

It is further to be seen in FIG. 6 that the light guides accommodated in the second space 80 are connected to a light source 104 via a line 106. Said light source is connected, in turn, to an image processing unit 108 which is connected to the image sensor 100, on the one hand, and to a monitor 110, on the other hand. The light source 104 can also be separate.

Figure 7:
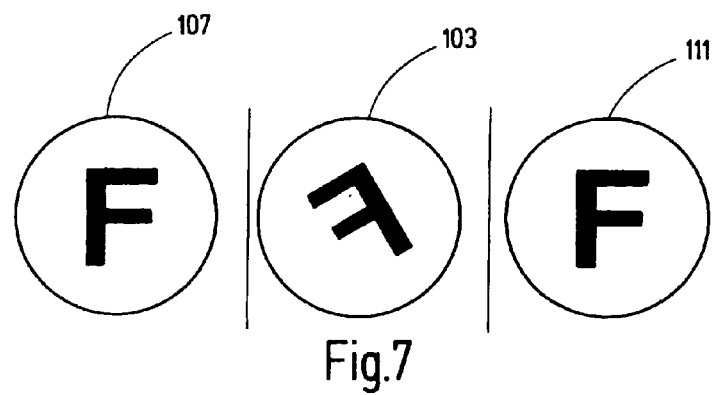
FIG. 7 shows the position of the images, once in the object field, then accordingly rotated in the image plane of the image sensor, and righted again on the monitor.

FIG. 6 depicts the course of a main beam 112 which emanates from an observation field 107, as is illustrated in FIG. 7 on the left hand side. The capital letter "F" is intended to be observed here. It is to be seen in FIG. 6 that the viewing direction deviates approximately by 20° from the 0° viewing direction, which runs along the longitudinal axis 94.

The main beam 112 traverses the cover glass 84 and the focusing lens 86 and is deflected at the first deflection face 90 onto the second deflection face 92 of the distal deflection prism 88. The main beam 112 is guided, in a fashion running in the middle and in the direction of the longitudinal axis 94, from the second deflection face 92 through the lens system 96. At the proximal end of the lens system 96, the main beam 112 enters the proximal deflection prism 98, is deflected by 90° and impinges on the active region 102 or the image plane 103 of the image sensor 100.

The previously described rotation produces an image on the image sensor 100 as illustrated in the middle of FIG. 7, that is to say "F" is reflected once in a reverse manner and rotated. In the image processing unit 108, the image is then appropriately processed so that an image appears on a monitor 110 as illustrated in FIG. 7 on the right hand side, that is to say corresponds to the original image.

Figure 8:
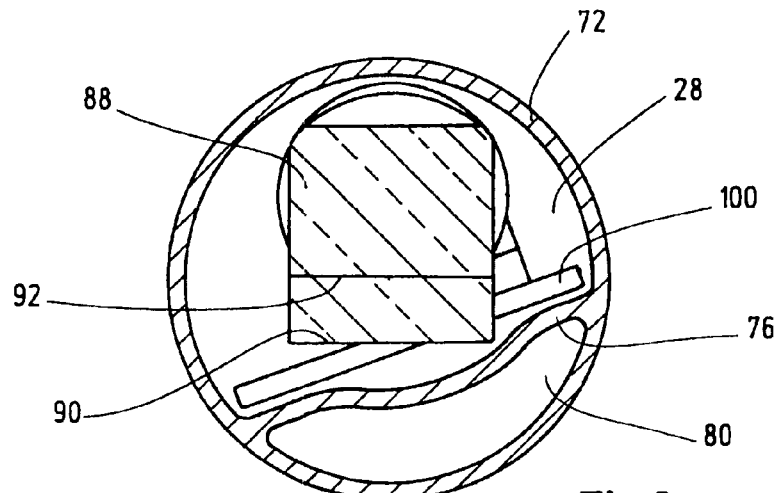
FIG. 8 shows a section along the line VIII-VIII in FIG. 6.
Figure 9:
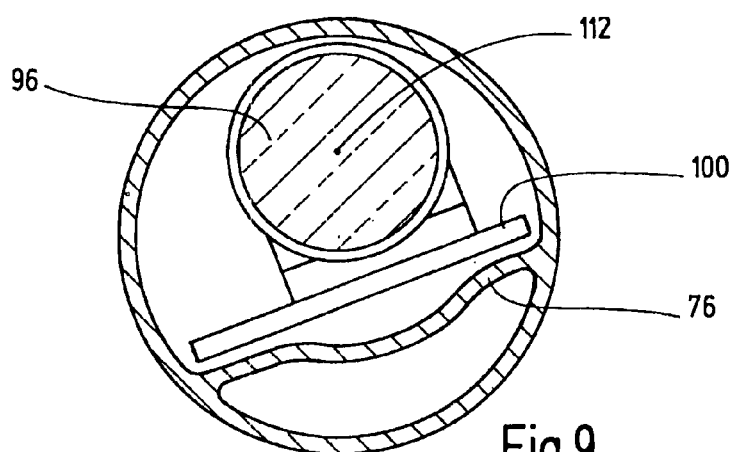
FIG. 9 shows a section along the line IX-IX in FIG. 6.
Figure 10:
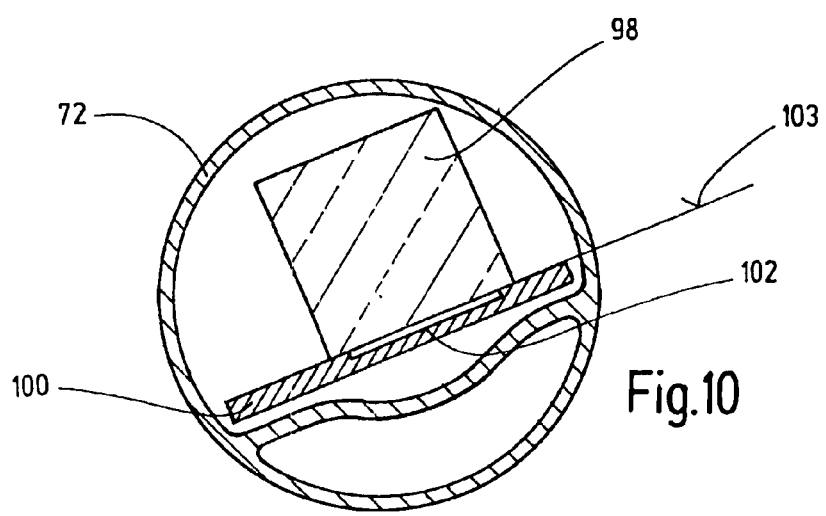
FIG. 10 shows a section along the line X-X in FIG. 6.

The sectional illustrations of FIGS. 8, 9 and 10 show the respective optical elements in a glass material, that is to say the distal deflection prism 88 with its first and second deflection faces 90 and 92, respectively. FIG. 9 shows the lens system 96 with the main beam 112. It is to be seen from FIG. 10 that the proximal deflection prism 98 covers the active region 102 of the image sensor 100, the image plane 103 being situated directly under the support face of the proximal deflection prism 98.

Figure 11:
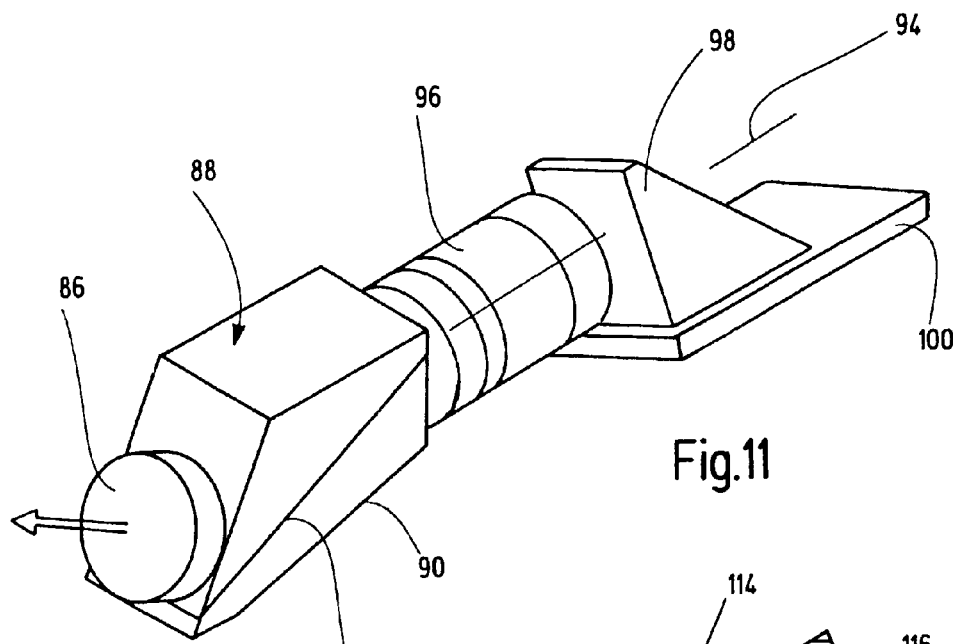
FIG. 11 shows a perspective illustration of the assembled optoelectronic imaging system.
Figure 12:
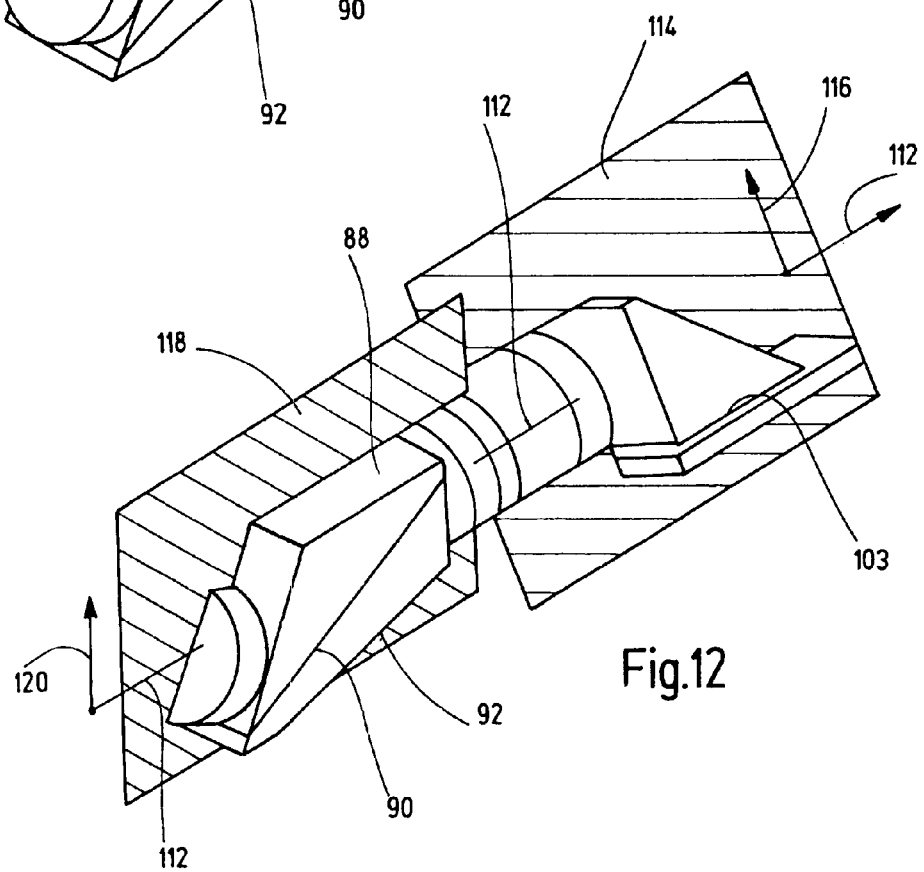
FIG. 12 shows an illustration corresponding to FIG. 11, the first and the second planes being illustrated together with the measure of the rotation relative to one another.

FIG. 11 illustrates these components once again, in a coherent manner, in a perspective view. The two planes are now illustrated in addition in FIG. 12, including how they are rotated relative to one another.

The first plane 114 is defined by the main beam 112 and an orthogonal 116 standing on the image plane 103.

The second plane 118 is likewise defined by the main beam 112 and a second orthogonal 120 which stands on the deflection faces 90, 92 of the distal deflection prism 88.

The first plane 114 is now rotated relative to the second plane 118 so that a situation, such as is illustrated in FIG. 5, is seen when looking onto the image sensor 100. A difference between the illustrations of FIG. 12 and FIG. 5 consists in that in FIG. 12 the image sensor 100 is arranged horizontally and not, as in FIG. 5, vertically. The basic principle is, however, the same for both configurations.

In the case of the second embodiment, it is possible to rotate the first and the second planes 114 and 118 relative to one another, or to arrange the deflection faces 90 and 92 of the distal deflection prism 88, so that a symmetrical sight cone 22 is produced, as is illustrated in FIG. 4.

What is claimed is:

1. An observation instrument, comprising
a hollow shaft having a midplane and a distal end region,
an optoelectronic imaging system arranged in said distal end region and having an image entrance side,
a distal deflection prism having deflection faces,
an optical lens system defining an optical path having a main beam,
an image sensor having an image plane comprising an active region which is situated asymmetrically relative to an outer contour of said image sensor,
said deflection faces of said distal deflection prism lead an image into said optical lens system which images said image onto said image plane of said image sensor,
a first plane defined by said main beam and a first orthogonal on said image plane, and
a second plane defined by said main beam and a second orthogonal on said deflection faces,
wherein said first plane and said second plane being rotated relative to one another about said main beam to an extent to produce a sight cone of said optical lens system which is symmetrical relative to said midplane of said hollow shaft and whose image area is situated fully in said active region of said image sensor.

2. The observation instrument of claim 1, wherein said image sensor is arranged vertically in said hollow shaft.

3. The observation instrument of claim 1, wherein said image sensor is arranged tilted to a longitudinal axis of said shaft, a proximal deflection prism being arranged between a proximal end of said lens system and said image sensor, said proximal deflection prism deflects an image emerging from said optical lens system onto said tilted image sensor.

4. The observation instrument of claim 1, wherein said image sensor is arranged horizontally and parallel to said longitudinal axis, and wherein said proximal deflection prism effects a 90° deflection of said image.

5. The observation instrument of claim 1, wherein said first plane and said second plane are rotated relative to one another to such an extent that said sight cone runs symmetrically relative to a longitudinal axis of said shaft.

6. The observation instrument of claim 1, wherein said image sensor is connected to an image processing unit, by means of which said image, which has been rotated by said rotation and, if appropriate, shifted, is righted again laterally and in terms of height.

7. The observation instrument of claim 1, wherein said optoelectronic imaging system is designed to produce a viewing direction deviated from a 0° viewing direction.

* * * * *